United States Patent
Barikosky

[19]

[11] Patent Number: 6,114,594

[45] Date of Patent: Sep. 5, 2000

[54] METHOD OF TREATING A WOUND USING DRESSING PRODUCT WITH CORE OF ALGINATE FIBERS

[75] Inventor: Michel Barikosky, Paris, France

[73] Assignee: Societe Precis, Nanterre, France

[21] Appl. No.: 08/794,736

[22] Filed: Feb. 3, 1997

Related U.S. Application Data

[63] Continuation of application No. 08/256,792, Nov. 4, 1994, abandoned, which is a continuation of application No. PCT/FR92/00063, Jan. 24, 1992.

[51] Int. Cl.[7] .................................................. A61F 13/20
[52] U.S. Cl. ............................ 604/367; 604/358; 602/43
[58] Field of Search ................................. 602/42–45, 47, 602/48, 53, 55; 604/310, 312, 383, 368, 378, 904, 304, 358, 367, 11

[56] References Cited

U.S. PATENT DOCUMENTS

| | | |
|---|---|---|
| 3,683,912 | 8/1972 | Olson et al. ............................ 128/285 |
| 3,835,856 | 9/1974 | Warncke ................................. 128/263 |
| 4,335,721 | 6/1982 | Matthews ............................... 128/285 |
| 5,197,945 | 3/1993 | Cole et al. ................................ 602/49 |
| 5,256,477 | 10/1993 | Mahoney ............................... 428/283 |
| 5,482,932 | 1/1996 | Thompson ............................... 514/54 |
| 5,968,001 | 10/1999 | Freeman ................................... 602/42 |
| 5,972,366 | 10/1999 | Haynes et al. .......................... 424/422 |
| 5,977,428 | 11/1999 | Bozigian et al. ......................... 602/48 |
| 5,998,692 | 12/1999 | Gilding ................................... 602/41 |

*Primary Examiner*—Corrine McDermott
*Assistant Examiner*—Cris L. Rodriguez
*Attorney, Agent, or Firm*—Vorys, Sater, Seymour and Pease LLP

[57] ABSTRACT

A core (1), in the form of a cylindrical pack, of a dressing is surrounded by a sleeve (2, 3) for holding the mechanical structure of the core. The sleeve (2), which may be comprised of threads (2, 3), is permeable to biological fluid of wounds and is biologically compatible with wounds. The dressing is very suitable for deep wounds, from which it can easily be removed.

11 Claims, 1 Drawing Sheet

METHOD OF TREATING A WOUND USING DRESSING PRODUCT WITH CORE OF ALGINATE FIBERS

This is a continuation of application Ser. No. 08/256,792 filed Nov. 4, 1994 abandoned which is a continuation of PCT/FR92/00063 filed Jan. 24, 1992).

The present invention relates to a dressing product or dressing for a wound with biological fluid, comprising, in a substantially cylindrical form, a core of fibres of a spinnable polymer.

Dressings of this type, generally in a pack form, are often used for weeping wounds, particularly deeps ones such as bleeding cavities like bedsores or other, post-operative wounds.

The polymer is often an alginate of a metal selected from the group of multivalent metals, with the exception of magnesium, and in particular alginate of calcium.

A wound, causes a loss of substance or of biological fluid (blood or exudate). When applied in a wound the dressing begins to absorb the oozing or bleeding biological fluid, the water molecules of the liquid becoming interspersed between the macromolecules of the alginate. Once swelled up by absorption, the dressing undergoes jellification due to ionic exchange. In the case of calcium alginate fibres they lose $Ca^{2+}$ to the biological fluid which gives up $Na^+$ ions to them. As the equilibrium between the calcium and the sodium takes place, the alginate fibres partially lose their crystalline structure. The jellification of the dressing from causes the wound to dry and prevents the dressing adhering to the subjacent tissues. However, jellification also causes splitting of and, more generally, a change in the integrity of the mechanical structure of the core which may make it difficult to remove from the wound without causing pain.

It is an object of the present invention to propose a dressing product of the aforementioned type with the capacity for absorption, retention and jellification intact but which can be easily and painlessly removed from a wound.

To this end, the dressing product in accordance with the present invention is characterized in that the core is surrounded by a holding sleeve of a structure permeable to biological fluid and biologically compatible with the wound.

Thus, while retaining the mechanical cohesion of the fibrillary core, the sleeve neither alters the action of absorption, dilation or jellification intended to extract the biological fluid, nor the action of retaining proteins and other cellular and bacterial waste which otherwise would hinder the scarring process.

The sleeve can be fibrous, having one thread or several. A single thread can connect the fibres of the core by meshing, in particular by so-called chain stitches, by winding, in particular with contiguous turns, for example. In the case of several threads they can, for instance, be meshed, plaited, twisted or woven around the core.

The sleeve can also be a porous sheath or openwork sheath. Biologically compatible covering materials include, for example, biologically compatible polymers such as polyesters, polyamides, viscose, and moreover, biologically absorbable polymers.

A polymer for the core can be a spinnable alginate of a metal selected from the group of multivalent metals, with the exception of magnesium.

In particular the alginate of calcium can be considered as a spinnable alginate.

The invention will be understood with the aid of the following description of several embodiments of the dressing product of the invention, with reference to the attached drawing in which.

Figure 1:
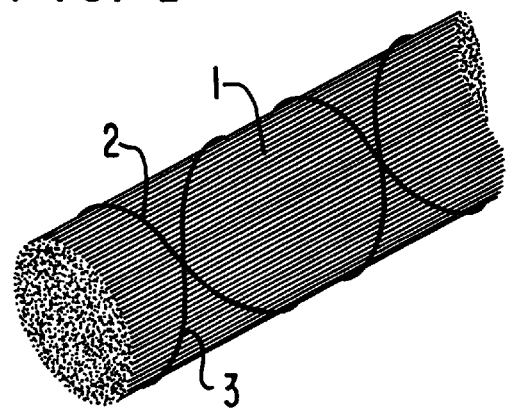
FIG. 1 illustrates a perspective view of a pack with two twisted holding threads.

The technique for producing a core, or pack, of polymer fibres, in particular of alginate, and more particularly calcium alginate, for a wound with biological fluid is now well proven and therefore does not need to be explained here, no more than the textured or untextured structure of such a pack. It merely needs to be stated that a pack is of a substantially cylindrical and elongated form. In order to avoid it splitting or disintegrating, in short, losing its mechanical cohesion, it is held, in the embodiment shown in the drawings, by a sleeve which is permeable to biological fluid and is biologically compatible with the wound to be dressed.

In the embodiment of FIG. 1, the pack 1 is held by two threads 2, 3 twisted around the pack in a relatively widely spaced manner.

Figure 2:
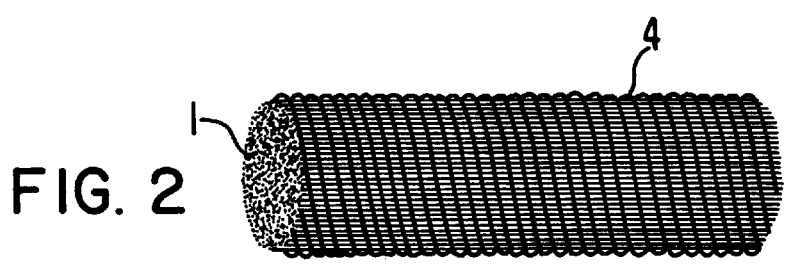
FIG. 2 illustrates a profile view of a pack with a holding thread wound in contiguous turns.

In the embodiment of FIG. 2, the pack 1 is held by a single thread 4 wound around it in almost contiguous turns.

Figure 3:
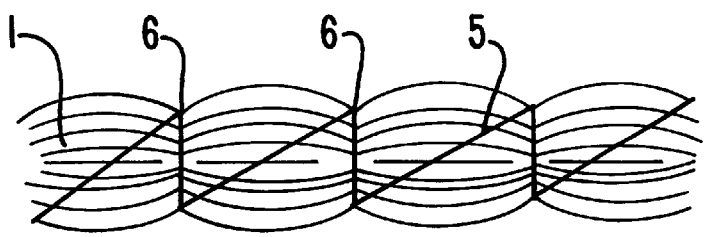
FIG. 3 illustrates a profile view of a pack with a holding thread meshed by chain stitches.

In the embodiment of FIG. 3, the pack 1 is held by a single thread 5 meshed by regularly-spaced chain stitches 6.

Figure 4:
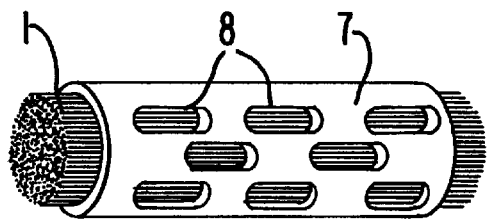
FIG. 4 illustrates a profile view of a pack with an openwork holding sheath.

In the embodiment of FIG. 4, the pack 1 extends inside a sheath-sleeve 7 pierced by holes 8 for the passage (drainage) of the biological fluid.

Figure 5:
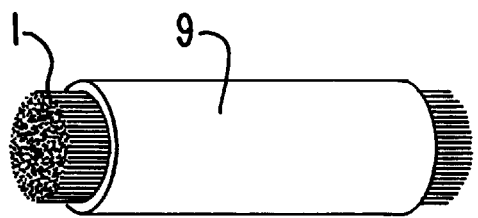
FIG. 5 illustrates a profile view of a pack with a porous holding sheath.

In the embodiment of FIG. 5, the pack 1 extends inside a sheath-sleeve 9 which has a porous wall for the passage of the biological fluid.

In all the embodiments described above, the biological fluid is still perfectly drained by the fibrillary pack. The threads or sheaths which surround it prevent it from splitting and from being in intimate contact with the wound. The substances trapped by the fibrillary gel are therefore no longer in contact with the wound. The pack can then be easily and painlessly removed from the wound.

What is claimed is:

1. A method of treating a wound, comprising:
   applying to the wound a dressing product including, in a substantially cylindrical form, a core of alginate fibres and a holding sleeve surrounding said core, said sleeve being permeable to biological fluid and biologically compatible with the wound, said sleeve further being constructed so as to substantially retain a capacity of the core to absorb and retain biological fluid and thereby undergo jellification, and so as to maintain sufficient structural integrity of the core, after jellification, to allow removal of the core from a wound without splitting and disintegration of the core.

2. A method according to claim 1, wherein the sleeve of the applied dressing product is fibrous.

3. A method according to claim 1, wherein the sleeve of the applied dressing product comprises a single thread wrapped around the core.

4. A method according to claim 1, wherein the sleeve of the applied dressing product comprises a plurality of threads each wrapped around the core.

5. A method according to claim 1, wherein the sleeve of the applied dressing product comprises a sheath.

6. A method according to claim 5, wherein the sheath has drainage holes formed therein.

7. A method according to claim 5, wherein the sheath is porous.

8. A method according to claim 1, wherein the sleeve of the applied dressing product consists of a single thread.

9. A method according to claim 1, wherein said sleeve of the applied dressing product is open at opposite ends thereof.

10. A method according to claim 9, wherein said core of the applied dressing product projects from the opposite ends of said sleeve.

11. A method according to claim 1, further comprising:
allowing the dressing product to remain applied to the wound for a time sufficient for the core to undergo jellification; and
removing the dressing product from the wound, the sleeve acting to prevent splitting and disintegration of the core during removal of the dressing product.

\* \* \* \* \*